(12) United States Patent
Moore et al.

(10) Patent No.: US 7,258,679 B2
(45) Date of Patent: Aug. 21, 2007

(54) INFLOW CONDUIT FOR VENTRICULAR ASSIST DEVICE

(75) Inventors: Daniel Richard Moore, Allison Park, PA (US); Christopher David Capone, Pittsburgh, PA (US); Marlin Stephen Heilman, Sarver, PA (US); Steve Andrew Kolenik, Leechburg, PA (US); Carl Michael Parisi, Kittanning, PA (US); Edward Karl Prem, Allison Park, PA (US); Richard Andrew Sofranko, Pittsburgh, PA (US)

(73) Assignee: Vascor, Inc., Pittsburgh, PA (US)

( * ) Notice: Subject to any disclaimer, the term of this patent is extended or adjusted under 35 U.S.C. 154(b) by 631 days.

(21) Appl. No.: 10/636,431

(22) Filed: Aug. 7, 2003

(65) Prior Publication Data

US 2006/0167333 A1 Jul. 27, 2006

Related U.S. Application Data

(60) Provisional application No. 60/402,453, filed on Aug. 9, 2002.

(51) Int. Cl.
*A61M 5/178* (2006.01)
(52) U.S. Cl. ................................. 604/164.11
(58) Field of Classification Search ............ 600/16–18; 604/164.01, 164.11
See application file for complete search history.

(56) References Cited

U.S. PATENT DOCUMENTS

| | | | |
|---|---|---|---|
| 4,023,468 A | 5/1977 | Poirier | |
| 4,086,665 A | 5/1978 | Poirier | |
| 5,511,958 A | 4/1996 | Chen et al. | |
| 5,599,173 A | 2/1997 | Chen et al. | |
| 5,613,935 A | 3/1997 | Jarvik | |
| 5,810,708 A | 9/1998 | Woodard et al. | |
| 5,827,220 A * | 10/1998 | Runge | 604/509 |
| 5,928,131 A | 7/1999 | Prem | |
| 5,947,892 A | 9/1999 | Benkowski et al. | |
| 5,980,448 A | 11/1999 | Heilman et al. | |
| 6,050,975 A | 4/2000 | Poirier | |
| 6,074,180 A | 6/2000 | Khanwilkar et al. | |
| 6,171,253 B1 | 1/2001 | Bullister et al. | |
| 6,186,999 B1 | 2/2001 | Chen | |
| 6,302,661 B1 | 10/2001 | Khanwilkar et al. | |
| 6,302,910 B1 | 10/2001 | Yamazaki et al. | |
| 6,319,231 B1 | 11/2001 | Andrultis | |
| 6,346,071 B1 | 2/2002 | Mussivand | |

OTHER PUBLICATIONS

"Novel Ventricular Apical Cannula: In-Vitro Evaluation Using Transparent, Compliant Ventricular Casts," A. S. Curtis, J. W. Zhongjun; R. L. Kormos, B. P. Griffith and J. F. Antaki, ASAIO Journal 1988; 44:M691-695.

(Continued)

*Primary Examiner*—Scott M. Getzow
(74) *Attorney, Agent, or Firm*—Buchanan Ingersoll & Rooney PC

(57) ABSTRACT

An inflow conduit of a ventricular assist device configured to prevent formation of recirculation and stagnation zones as well as collapse due to external forces or pump induced suction can be rigid and have a funnel like shape with an elbow to accommodate a patient anatomy. Stiffening elements and pressure sensing devices can also be provided associated with the inflow conduit.

18 Claims, 13 Drawing Sheets

OTHER PUBLICATIONS

"Mechanical Bloodtrauma: An Overview," L. J. Wurzinger, R. Optiz. H. Eckstein, Angeiologie 1986;38(3):81-97.

Platelet and Coagulation Parameters Following Millisecond Exposure to Laminar Shear Stress, L. J. Wurzinger, R. Optiz, P. Blasberg, H. Schmid-Schonbein, Thromb Haemost 1985;54(2):381-386.

"Towards A Concept of Thrombosis in Accelerated Flow: Rheology, Fluid Dynamics, and Biochemistry," L. J. Wurzing, P. Blasber, H. Schmid-Schonbein, Biotheology, 22;437-449, 1985.

"Shear Induced Platlet Activation: A Critical Reappraisal," L. J. Wurzing, R. Opitz, M. Wolf, H. Schmid-Schonbein, Biorheology, 22;399-413, 1985.

Red Blood Cell Damage By Shear Stress, L. B. Leverett, J. D. Hellums, C. P. Alfrey, E. C. Lynch, Biophysical Journal, 1972;12(3)257-273.

"Morphological, biochemical, and functional changes in human platelets subjected to shear stress," C. H. Brown, L. B. Leverett, C. W. Lewis, C. P. Alfrey, J. D. Hellums, J Lab Clin Med 80(1):462-471, 1975.

* cited by examiner

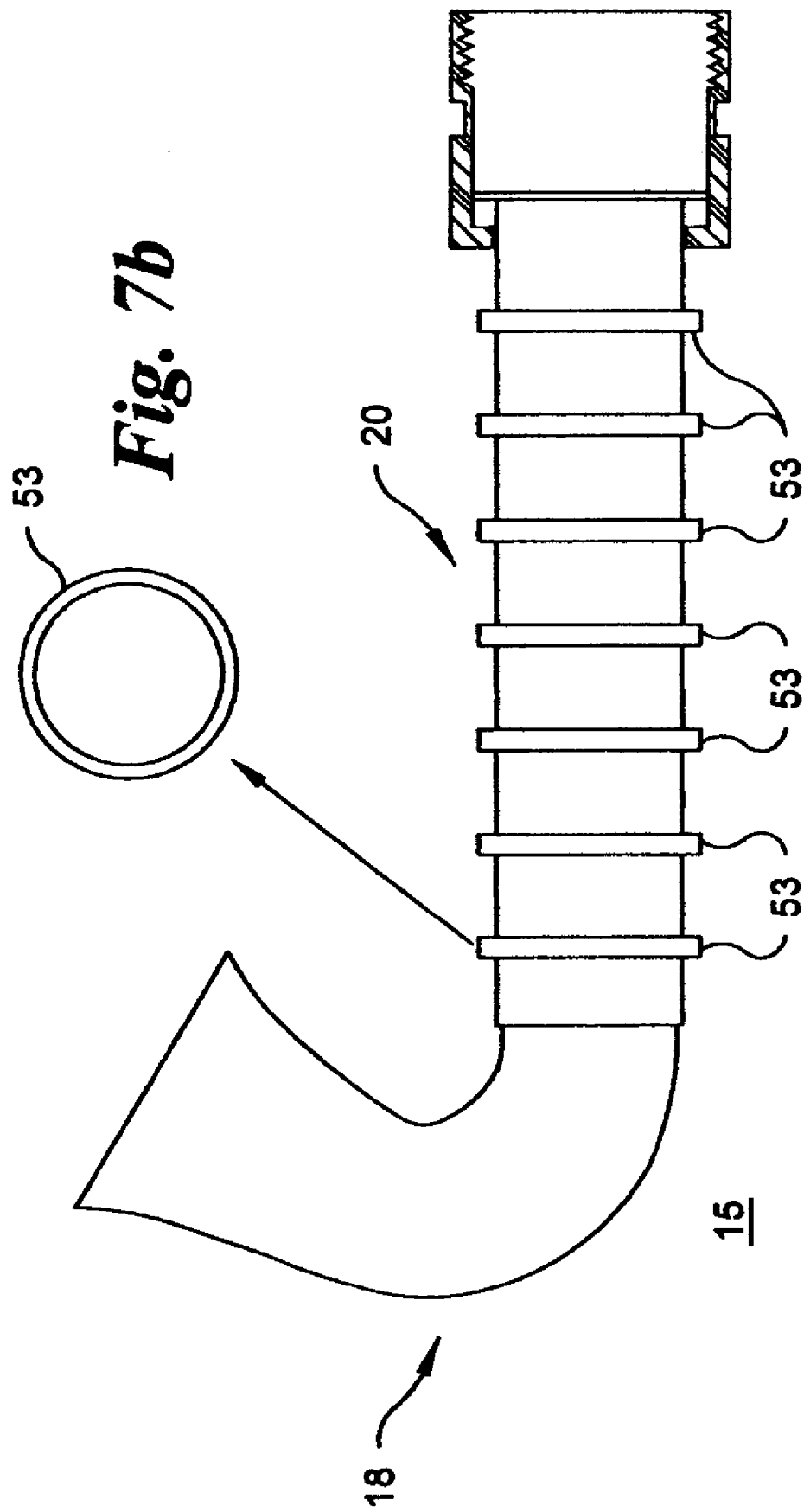

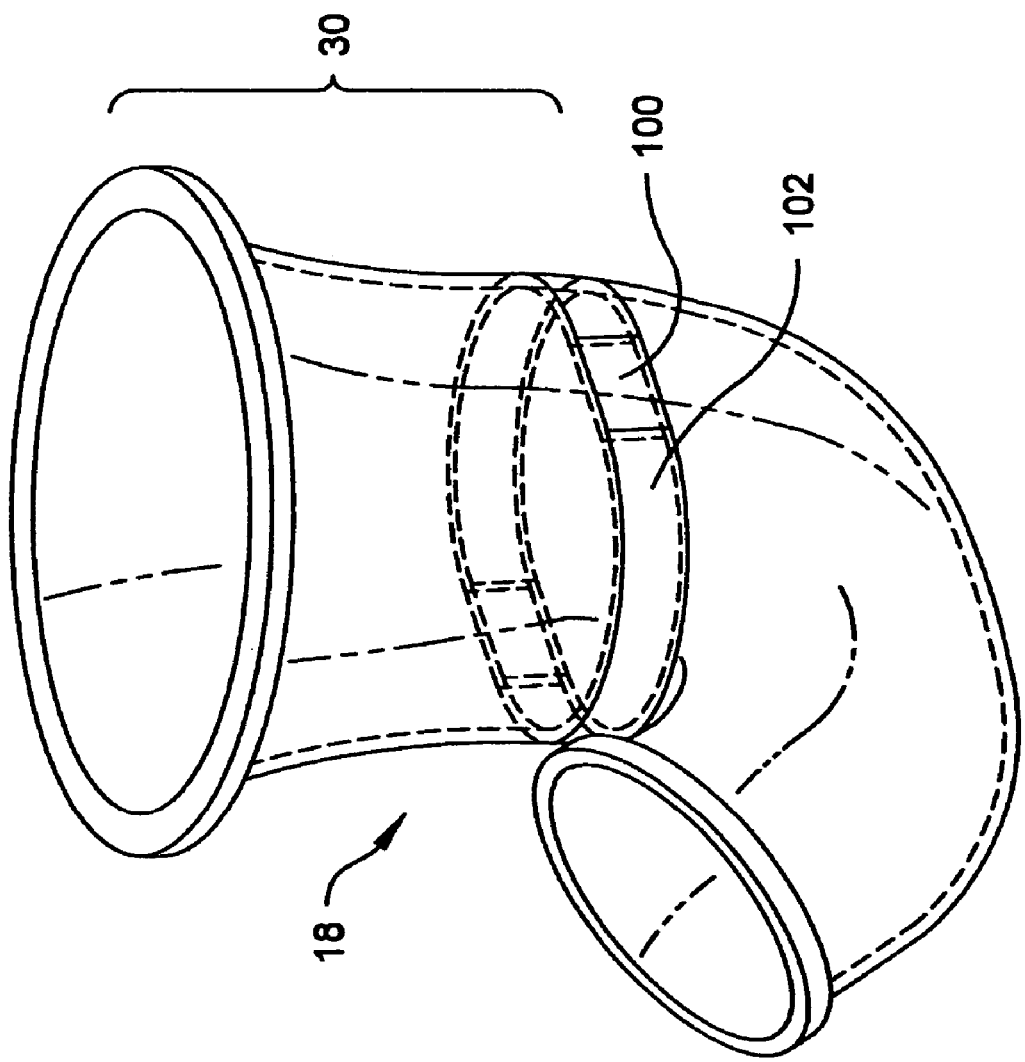

INFLOW CONDUIT FOR VENTRICULAR ASSIST DEVICE

RELATED APPLICATIONS

This application claims priority to U.S. Provisional Patent Application Ser. No. 60/402,453, filed Aug. 9, 2002.

BACKGROUND

An estimated 4.8 million Americans suffer from congestive heart failure (CHF). Many of these persons are unresponsive to pharmacological intervention and could benefit from a heart transplant. As a result of the current shortage of donor hearts, implantable blood pumps have gradually evolved into a viable treatment option for these persons. Over the past 30 years, many devices have been developed that either replace the entire heart or assist the heart.

In a diseased state, one or both of the ventricles of the heart can become greatly weakened to an extent that mechanical intervention is needed to keep a patient alive. In some instances, the entire heart is removed and replaced with a total artificial heart while in other cases a device that assists the heart is used. A blood pump used for assist is commonly referred to as a ventricular assist device or VAD.

Although either of the ventricles of the human heart may function in a weakened state, it is the left ventricle that is primarily treated for insufficient pumping. Normally, blood enters the left ventricle through the mitral valve and, during heart systole, the blood is ejected through the aortic valve and into the aorta by the squeezing action of the left ventricle. To assist a failing left ventricle, a VAD is typically attached between the apex of the left ventricle and the thoracic aorta. In this way, blood entering the left ventricle may either be ejected through the aortic valve by the ventricle or pass through the VAD.

Ventricular assistance has been performed by a variety of blood pump designs. The majority of the early VADs pumped blood in a pulsatile manner. In this case, the VAD has an internal sac situated between two heart valves. The sac is typically allowed to passively fill with blood, then the VAD pumping mechanism squeezes the sac, ejecting the blood into the patient's aorta. Patents such as U.S. Pat. Nos. 5,599,173, 5,980,448 and 4,023,468 teach devices that move blood in this manner. These pulsatile VADs are typically large and can only be used as an implantable treatment option for patients with a large body surface area, such as a large man. In addition, reliability issues exist due to the heart valves that are required for pulsatile pumping.

More recently, continuous flow pumps are being developed to address the size and reliability requirements. VADs such as described in U.S. Pat. Nos. 5,947,892, 5,613,935, 6,074,180, 5,928,131, and 6,050,975 operate in this fashion. These pumps are smaller than their pulsatile counterparts and can be inherently more reliable. VADs having a magnetically suspended rotor, such as those described in U.S. Pat. Nos. 5,928,131, 6,050,975, 6,074,180, and 6,302,661, can have only one moving part, the pump rotor.

The connection of a VAD to the human anatomy typically requires two conduits or tubes: an inflow conduit to allow blood into the VAD and an outflow conduit to pass the pressurized blood exiting the VAD to the patient's aorta. Although these necessary components are required for nearly all VAD implantations, they are typically overlooked as components that affect VAD performance, in particular their propensity for inducing blood damage.

Previous work has disclosed various connection schemes, such as described in U.S. Pat. Nos. 4,086,665 and 5,511,958, while others have dealt with the conduits as part of an assist device design such as described in U.S. Pat. Nos. 6,346,071 and 6,319,231. Although the amount of published literature is limited, studies examining the affect of inflow conduit tip shape have shown its importance, for example "Novel ventricular apical cannula in vitro evaluation using transparent, compliant ventricular casts", by Curtis et al. This work has clearly shown that it is possible to substantially improve the flow pattern immediately adjacent to the conduit tip through improved tip design.

For a continuous flow pump, the inflow conduit is subjected to additional pressure swings not present for pulsatile pumps. The passive filling of pulsatile pumps maintains an inflow conduit pressure that closely matches the pressure in the left ventricle. This is due to the valve that is typically positioned between the inflow conduit and the blood pump chamber For continuous flow pumps, no valve is present between the inflow conduit and blood pump. Consequently, any pressures generated upstream of the blood pump impeller blades are reflected within the inflow conduit and the left ventricle.

A low-flow and low-pressure condition is possible for continuous flow pumps if the pump continues to operate at a given speed and the left ventricle has an insufficient volume of blood available for pumping. In this instance, the pressure in the left ventricle and the inflow conduit drops quickly and both are subjected to a negative pressure. This negative pressure can cause the ventricle and/or inflow conduit to collapse. If the pump speed is not reduced, the collapse can continue and the negative pressure can cause gases to be drawn out of the blood. This phenomenon is known as cavitation and has been shown to cause blood damage.

Most of the currently available continuous flow pumps use manual control to govern the assist level of the pump. To avoid collapse and low pressures mentioned above, the pump assist level is typically set to a low level in order to avoid damaging the blood. However, this method of pump control can result in an insufficient level of assist for the patient. A preferred method for controlling a blood pump can be to measure some physiologic parameter, such as left ventricular pressure or heart size, and use that parameter to govern pump operation. Such a control scheme has been described in U.S. Pat. No. 5,928,131 for continuous flow pumps.

A pressure sensing scheme has been disclosed in U.S. Pat. No. 6,171,253 in which geometric changes in a blood carrying conduit are sensed and used as an indication of blood pressure within the blood carrying conduit. A section of the blood carrying conduit is somewhat flattened to provide a focal point for any pressure-induced shape change of the conduit. A set of strain gauges can then be used to measure the flexure of the flattened portion when pressure changes in the conduit occur. In another embodiment, the flexure can also be measured using an optical sensor that detects how far the flattened portion has moved. Yet another embodiment uses two fluid compartments to measure changes in the geometry in the flattened region of the conduit. One of the fluid compartments is partially bounded by the flattened portion of the conduit. The second compartment is situated adjacent to the first compartment with a flexible diaphragm between the two. Monitoring the pressure in the second compartment allows indirect sensing of the pressure with in the blood carrying conduit, since changes in the blood pressure within the conduit produce pressure changes within the first fluid compartment and consequently the second fluid compartment.

Several inventions have been disclosed which obviate the need for an inflow conduit, U.S. Pat. Nos. 4,944,078 and 5,507,629. This VAD is intended for placement within the left ventricular volume, thus occupying the space that is normally filled with blood. This placement negates the need for an inflow conduit, thus removing an implanted component that may cause blood damage or have other possible failure modes. However, the pump inlet is very close to the heart tissue and it is likely that negative pressure spikes could quickly develop for this VAD. The inflow conduits normally used have a portion of vascular graft incorporated within their design. Strictly speaking, collapse of an inflow conduit is undesirable, but with the VAD in U.S. Pat. No. 5,507,629 no compliant graft is positioned between the heart tissue and the pump. Consequently, any negative pressure spike will be solely imposed upon the heart tissue, making the likelihood of drawing heart tissue into the pump much greater.

U.S. Pat. No. 5,599,173 describes the structuring of the inflow channel of a VAD to produce beneficial flow patterns in the blood sac of a VAD. The inflow channel of the above invention is tapered to direct the blood entering the VAD toward the annular wall of the sac. This produces uniform flow that minimizes the chance of thrombus formation on the blood-contacting surface of the sac.

A custom inflow conduit is needed that conforms to the patient's anatomy, allows the blood entering the blood pump to do so in a stagnation- and recirculation-free manner, and prevents suction-induced collapse.

SUMMARY

According to the invention an inflow conduit can be provided to avoid the damage-free flow of blood from a left ventricle into a blood pump. The inflow conduit for a ventricular assist device can have features to avoid the formation of recirculation and stagnation zones as well as collapse of the conduit due to external forces or pump-induced suction.

The inflow conduit can be a tube with a cannula for attachment to the left ventricular apex of the heart and an end for attachment to the blood pump. The cannula can be rigid, can have a funnel-like shape, and can have an integral elbow that accommodates a patient's anatomy. A length of woven or knitted polyester can be attached to the cannula and can provide an adjustable section to the inflow conduit that allows freedom of anatomical placement of the pump relative to the heart. The topology of the cannula can be designed to eliminate stagnation and recirculation within the conduit.

Other features can be provided to avoid collapse of the inflow conduit due to various loading conditions. In particular, stiffening elements can be added to the polyester portion of the inflow conduit to prevent collapse of the conduit. The elements may be individual stiffening rings or a segmented assembly that can be rigid and adjustable. It is also possible to incorporate a pressure sensing means as a portion of the inflow conduit to control the operation of a blood pump. In addition, the sewing cuff used for attachment of the inflow conduit to the heart can also be used as a defibrillation electrode.

Other details, objects, and advantages of the invention will become apparent from the following detailed description and the accompanying drawings figures of certain embodiments thereof.

BRIEF DESCRIPTION OF THE DRAWINGS

A more complete understanding of the invention can be obtained by considering the following detailed description in conjunction with the accompanying drawings figures, in which:

FIGS. 7a-7b illustrate an embodiment of a cannula having reinforcing ring members;

FIGS. 11a-11d show another embodiment of reinforcing armor for a cannula;

FIG. 12 is a perspective view of a cannula according to the invention which can include a force measuring element;

DETAILED DESCRIPTION

Figure 1:
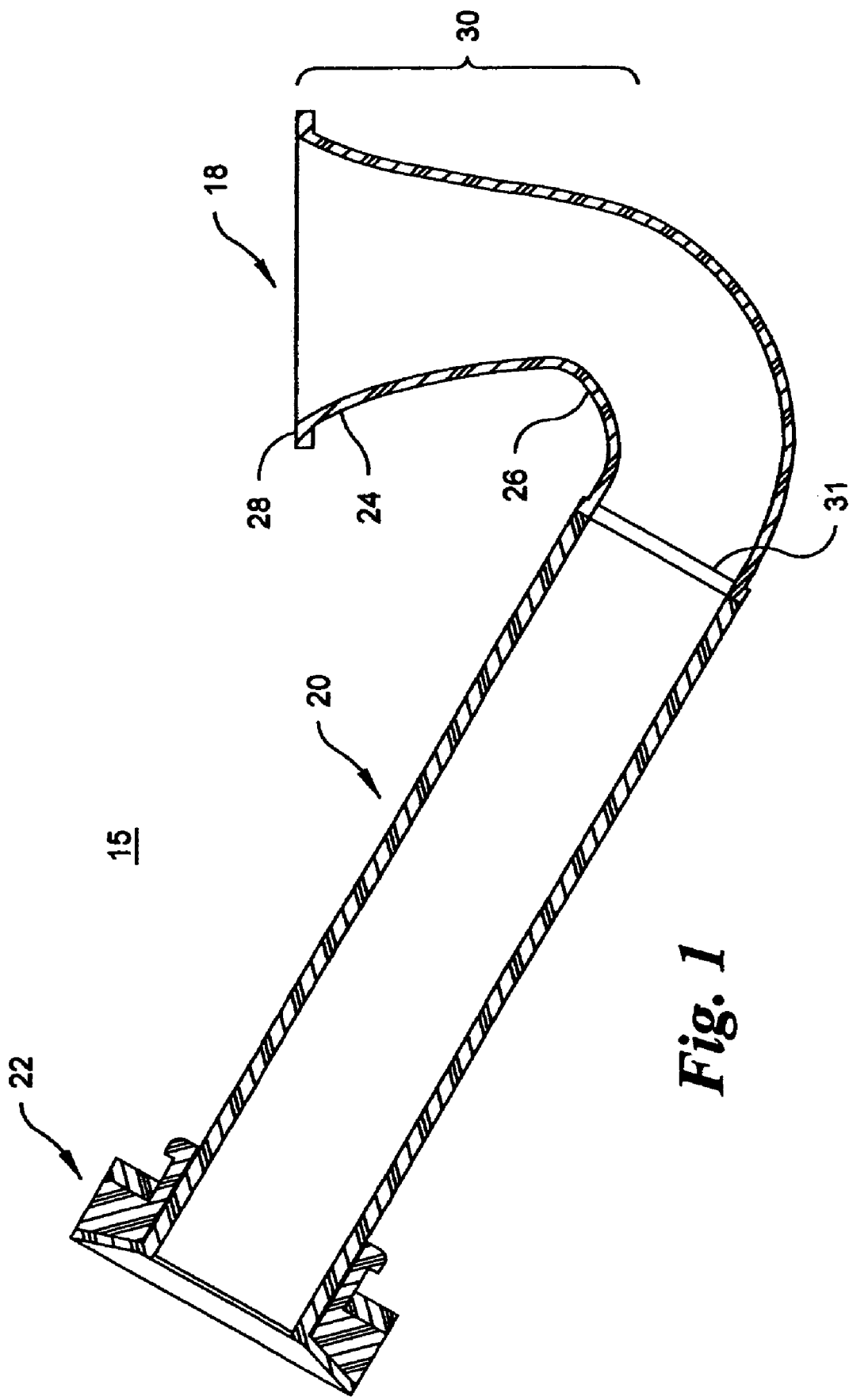
FIG. 1 is a cross sectional view of an embodiment of an apical cannula according to the invention.

Referring now to the drawing figures, wherein like reference numbers refer to similar parts throughout the several views, a cross section of an embodiment of an inflow conduit 15 is shown in FIG. 1. The inflow conduit 15 can be configured to provide stagnation-and recirculation-free movement of blood from a patient's left ventricle to a blood pump. The inflow conduit 15 can have three primary portions: an apical cannula 18, a graft portion 20, and a blood pump connector 22. As described hereinafter, each of these portions can have certain features that may be employed individually or cumulatively.

Although variations in the method of connecting a VAD to the patient's body have been tried, VADs are typically attached to the apex of the patient's left ventricle and the thoracic aorta. To facilitate this type of attachment, the apex is cored using a circular cutting tool that allows the removal of a portion of the heart wall. A portion of the inflow conduit 15 can then be inserted into the hole and fastened to the ventricle. For the present invention, the portion of the inflow conduit 15 that passes through the apical hole and can be attached to the heart is referred to as the apical cannula 18.

A distal portion 24 of the apical cannula above the bend 26 can have inner and outer surfaces geometrically adapted for blood flow shaping and anatomical fit, respectively. In one embodiment, the length of the distal portion 24 of the apical cannula 18 above the bend 24 can be approximately 2.0 cm. However, this length can vary depending on the wall thickness of the patient's left ventricle. The tip 28 of the apical cannula 18 can have a circular cross section, for example, with a diameter of 1.8 cm in one preferred embodiment of the invention. Other tip diameters are possible depending, once again, on the anatomical constraints of the patient. For instance, the preferred diameter listed above is intended for an adult patient. An inflow conduit 15 intended for a very small adult or a child is somewhat smaller.

Moving from the tip 28 of the apical cannula 18 toward the bend, the apical cannula 18 diameter can decrease and the cross-sectional shape can be noncircular. The cross-sectional shape through the bend 24 can be noncircular and can transition back to a circular shape as the graft portion 20 of the conduit is approached. The graft portion 20 can be made from a polyester material. The precise topology of the apical cannula 18 governs the manner in which blood passes across the bend 26.

To determine the topology of the apical cannula 18, for example, an initial cannula centerline trajectory that fits an adult anatomy was determined. This evaluation was made using solid modeling computer software that is typically used for the design of mechanisms. For development of the current apparatus, solid models of the thoracic cavity of a male and female were developed. In each instance, a rib cage, aorta, and left ventricle were constructed from the Visual Human Project data. This data was gathered from computed topography scans, magnetic resonance images and photographs of two human cadavers. The data can be purchased from Research Systems Inc. and comes with software to view the data.

Assuming a blood pump like that described in U.S. Pat. No. 5,928,131 was to be used, two different pump locations relative to the anatomy were considered. In the one instance, the pump is placed in the patient's abdominal cavity while in the other it is placed in the thorax. If a suitably long graft portion 20 is used, either pump placement may be used for a single apical cannula 18 topology. However, in the example for the current apparatus, two basic configurations were chosen. In one instance, it is assumed that the bend 26 in the apical cannula 18 spans a sixty-degree angle, while in another a one hundred twenty-degree angle is used.

A key consideration in the successful implementation of the inflow conduit 15 is the manner in which the inflow conduit 15 fits into and is attached to the left ventricle. The fit of the apical cannula portion 18 is preferably snug without imparting excessive pressure to the surrounding heart muscle. As stated above, a cylindrical plug of tissue can be cut and removed from the apex of the left ventricle in order to accommodate the apical cannula 18. A generally straight region 30, i.e., the region between the bend 26 and the tip 28 of the apical cannula 18 can be tapered to manipulate the blood flowing through it. The diameter of the hole cored into the left ventricular apex can be chosen to relatively closely match the diameter of the straight region of the apical cannula 18 between the tip 28 and the bend 26. For example, the diameter of the hole can be the average of the diameter of each end of the straight region 30 of the apical cannula 18.

The diameter of the tip 28 of the apical cannula 18 can have a larger diameter than the hole cut into the ventricle for multiple reasons. For example, if the diameters are sufficiently close, the tip 28 of the apical cannula 18 can be easily forced through the smaller hole in the apex. Bench tests were conducted using cadaveric tissue to determine an approximate ratio of tip diameter to apical hole diameter. It can be preferable that the diameter of the tip 28 does not significantly exceed the median diameter of the straight region 30 of the apical cannula 18, e.g., by not more than about 0.5 cm. This size restriction eliminates the need for a special tool to insert the apical cannula 18 into the heart.

A large diameter can help also to avoid flow stagnation within the left ventricle and around the tip 28 of the apical cannula 18. Another consideration affecting the diameter of the tip 28 is the minimization of the pressure drop across the entire inflow conduit 15. The pressure drop across the inflow conduit 15, as well as an outflow conduit (not shown), must be factored in to the overall pumping requirements of a VAD. Any required increases in pump performance resulting from the design of the inflow conduit 15 can ultimately lead to increases in pump size or increased power consumption, the second of which shortens the charge time of any implanted batteries. Thus, minimizing the pressure drop is a preferred outcome for any inflow conduit 15 design.

Figure 2B:
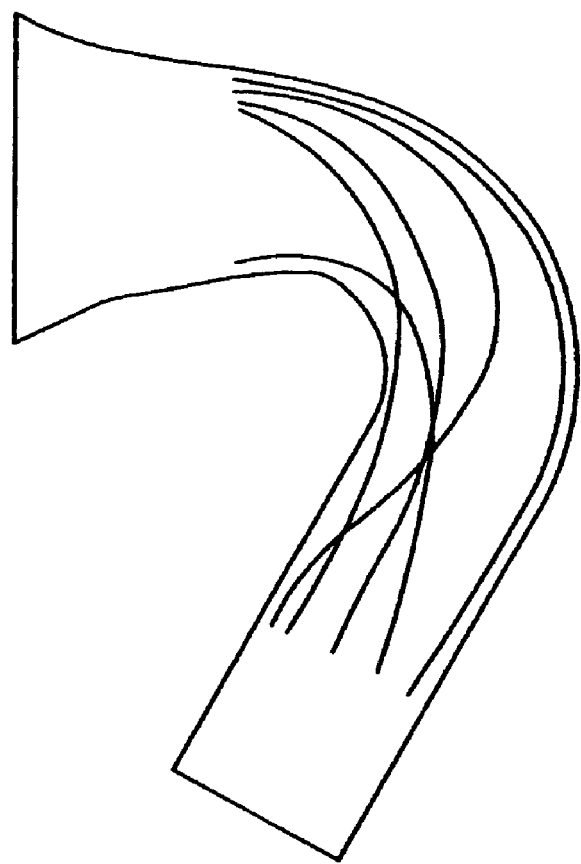
FIGS. 2a and 2b illustrate flow characteristics of blood through curved cannulas.
Figure 2A:
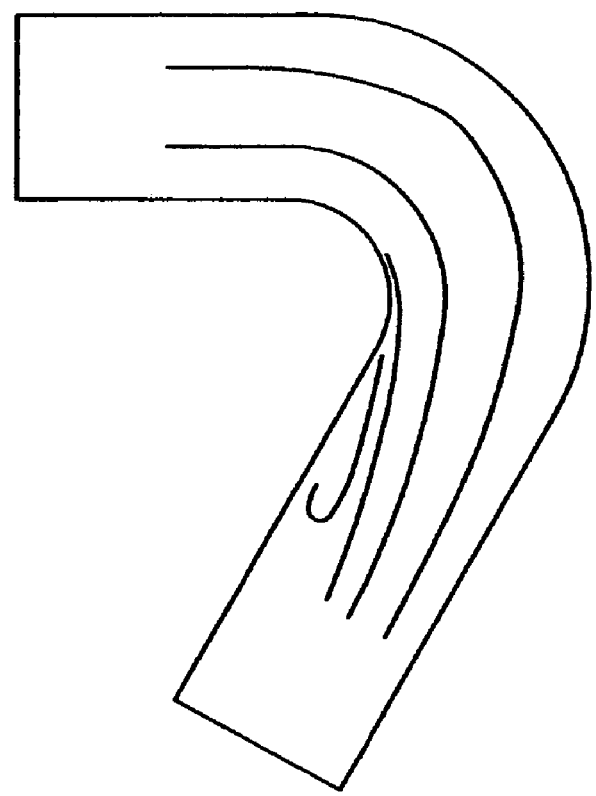
Figure 3C:
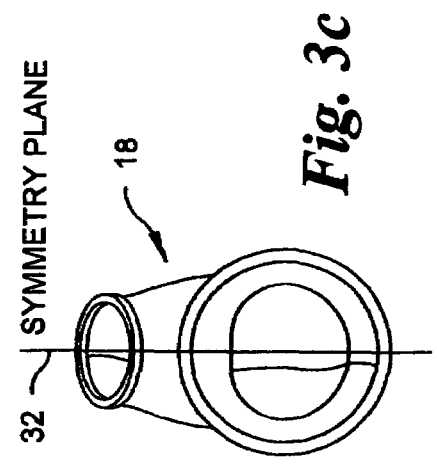
FIGS. 3a-3d illustrate symmetry planes.
Figure 3D:
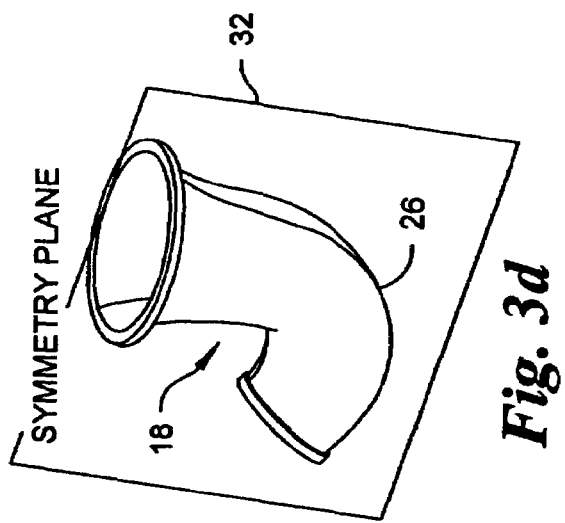
Figure 3A:
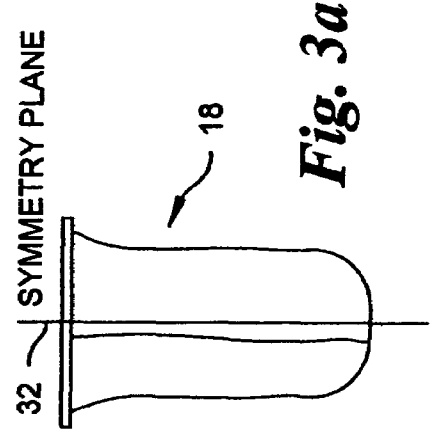
Figure 3B:
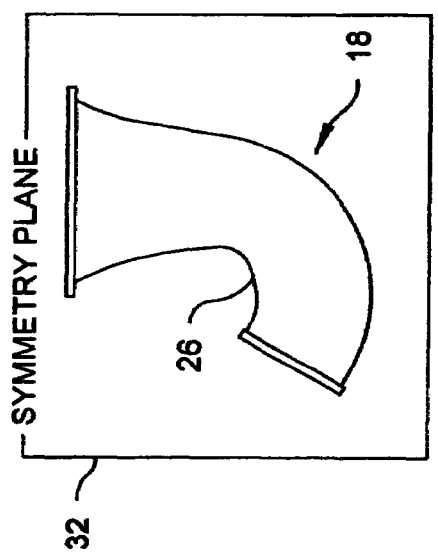
Figure 4:
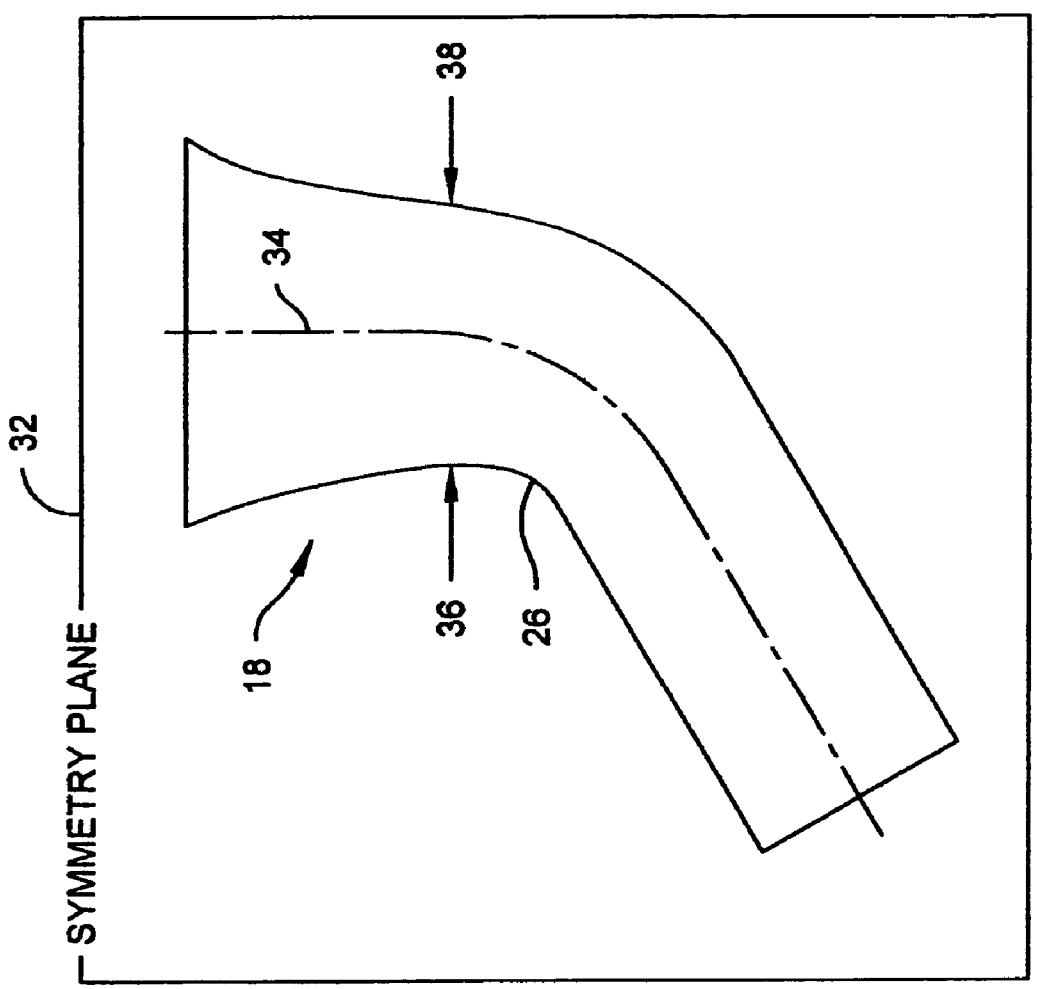
FIG. 4 is a cross sectional view through a symmetry plane showing the gradual changes in the cross sectional shape which occurs through the bend in the cannula.
Figure 5:
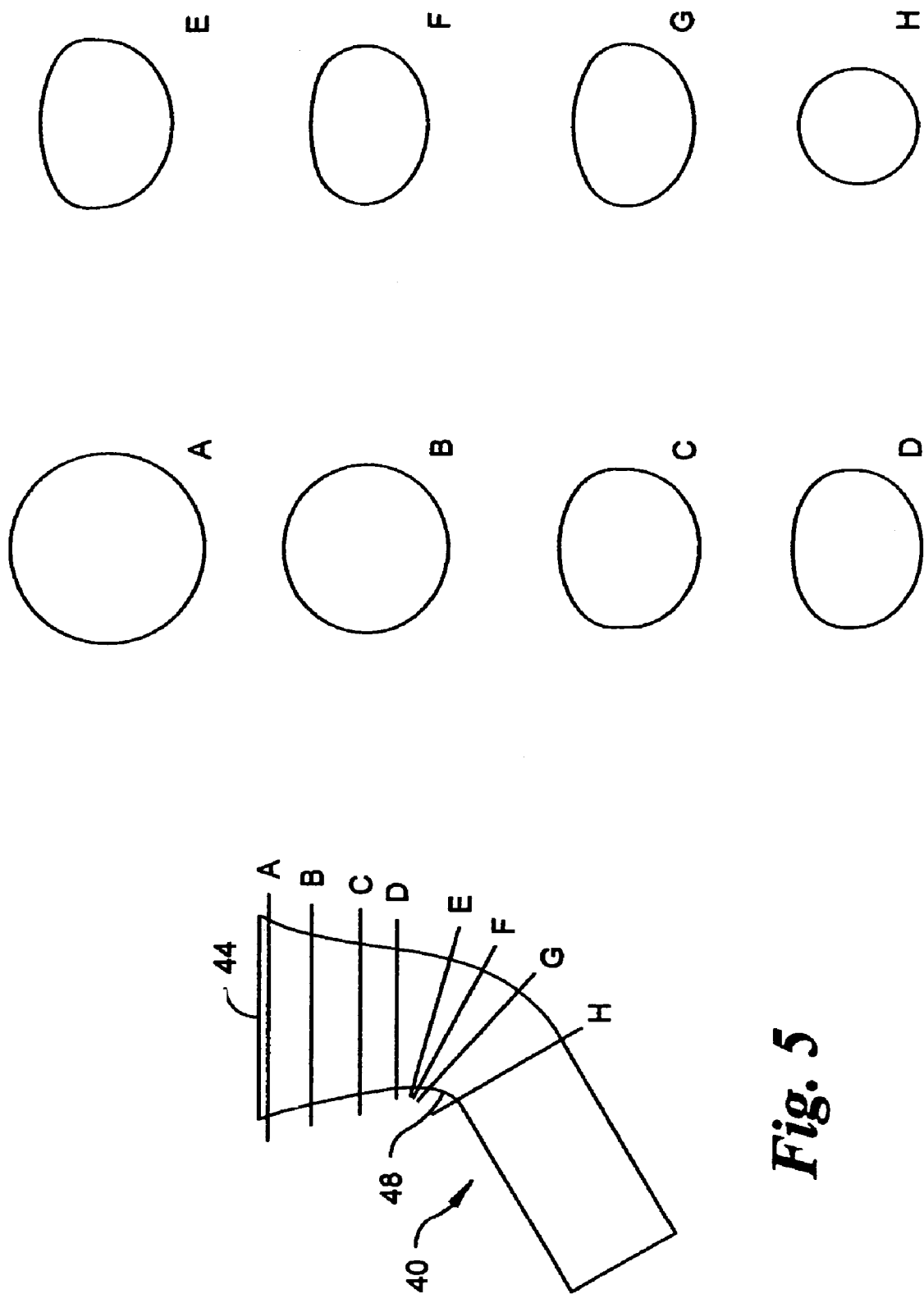
FIGS. 5A-5H are cross sectional views taken through lines A-H, respectively.
Figure 6:
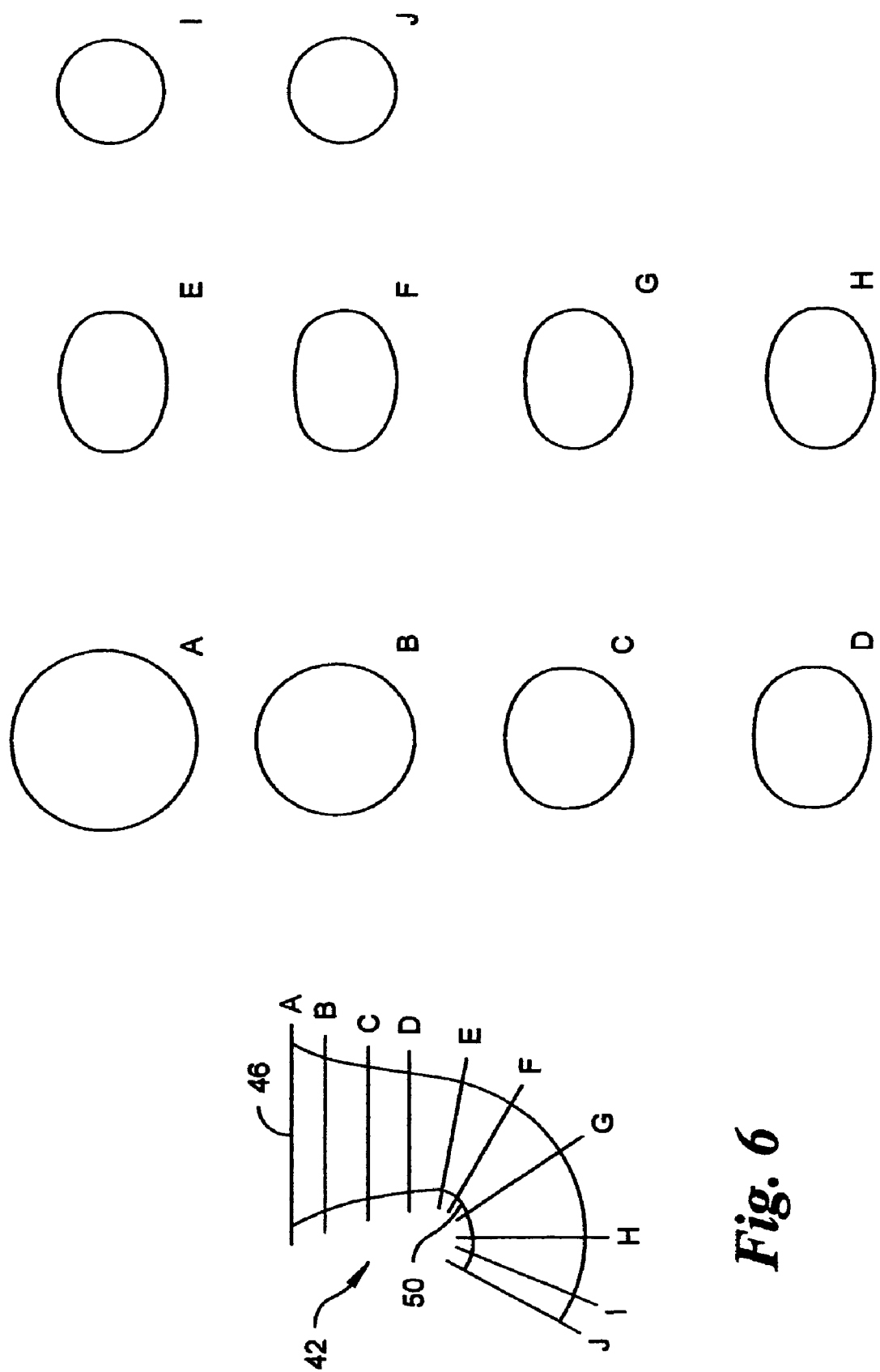
FIGS. 6A-6J similarly are cross sectional views taken through lines A through J.

Due to the anatomical constraints of the human anatomy, the apical cannula 18 can have a preformed bend 26 that is preferably rigid. As illustrated in FIG. 2a, when a tube having a constant circular cross-section is bent around a sixty-degree or one hundred twenty-degree angle, considerable flow separation occurs downstream of the bend at the inner radius. For this case, the stagnation and recirculation resulting from the flow separation create a zone that is likely to encourage the formation of blood clots and the deposition of tissue on the conduit wall. However, if a sufficiently large cannula bend radius is used, the presence of flow separation can be avoided or at least lessened. Nevertheless, as stated above, the bend radius of the inflow conduit cannula cannot be overly large due to anatomical constraints of the human body. Consequently, other methods, such as described hereinafter, can be used to prevent, or at least inhibit, separation and recirculation after the bend 26 in the axial cannula 18, as illustrated in FIG. 2b.

Embodiments of an apical cannula 18 according to the present invention can have a symmetry plane 32 associated with its geometry. FIGS. 3a-3d illustrate the symmetry plane 32 from four different angles. The bend 26 in the apical cannula 18 occurs within the plane of symmetry 32 and the descriptions of the apical cannula 18 topology hereinafter refer to the symmetry plane 32.

The topology for sixty-and one hundred twenty-degree versions of the apical cannula 18 can follow a general trend. In making a transition from a large cross-section to a smaller cross-section, the flow becomes compressed as it advances along the apical cannula 18. The manner it which the flow is compressed to prevent flow separation is related to the angle of the bend 26 and the positioning of the bend 26 with respect to the flow path. Referring to FIGS. 4 through 6J, as the point of view is moved along the cannula centerline 34, the cross-sectional shape of the apical cannula 18 gradually changes from a circle to a flattened oval. This shape change continues through the bend 26 in the apical cannula 18, after which a transition back to a circular cross-section is made. Flattening of the circular cross-section initially occurs along the top 36 and bottom 38 of the apical cannula 18, rather than on the sides. This narrowing is symmetric about the symmetry plane 32 of the apical cannula 18 and results in a decrease in the apical cannula 18 diameter in the bend region 26. As the bend 26 in the apical cannula 18 is completed, the width of the apical cannula 18 is reduced such that a circular cross-section is achieved. This dimensional change occurs perpendicular to the symmetry plane 32. In this way, the transition from a large circular cross-section to a smaller circular cross-section is made in a fashion that inhibits flow separation after the bend 26. It can be important that the top-to-bottom flattening occurs through the bend 26, rather than a change in width or side-to-side flattening.

In FIGS. 5A-5H, a one hundred twenty-degree bend apical cannula 40 is depicted, whereas a sixty-degree bend apical cannula 42 is depicted in FIGS. 6A-6J. In both cases, the apical cannula 40, 42 can be circular in cross-section at the tip 44, 46 and after the bend 48, 50. In both cases, a top-to-bottom flattening occurs through the bend 48, 50 with a subsequent reduction in conduit width. In FIGS. 5A-5H and 6A-6H, multiple cross-sections views along the apical cannula 40, 42 are illustrated to show the changes in the cross-sectional shape of the apical cannula 40, 42, from one end to the other.

This method of cross-sectional change through a bend inhibits the flow separation that typically occurs following a bend in a conduit of circular cross-section. The initial decrease of the in-plane conduit thickness tends to squeeze the flow, thus inhibiting flow separation after the bend. Simultaneously, the out-of-plane cannula width decreases. This dimensional change compresses two symmetrical counter-rotating flow patterns and further helps provide adequate washing after the cannula bend. The precise dimensional variation is different for the sixty-degree bend cannula versus the one hundred twenty-degree bend cannula. However, the underlying mechanism of flow manipulation follows a similar trend. Other similar configurations are possible for various cannula diameters, trajectories, and bend angles.

The solid model of the apical cannula portion 18 of the inflow conduit 15 was developed from an approximate trajectory traced between the blood pump and the heart. Factors such as the estimated length of the portion passing through the heart wall, the tip 28 diameter and the diameter of the end portion 31 of the cannula 18, which attaches to the graft portion 20 of the inflow conduit 18, were incorporated into the design. These dimensions were determined from published literature and measurements of the Visual Human data.

A completed design was then verified against the Visual Human model for overall fit. The theoretical performance of the design was then evaluated using computational fluid dynamics (CFD) software. The design was checked for zones of recirculation or stagnation and then the solid model reworked to eliminate problem areas.

Although substantial research has been conducted in the field of blood damage (or hemolysis), considerable debate continues regarding the exact conditions for which hemolysis occurs or which theoretical model accurately predicts if it will occur. Generally speaking, the level of shear imparted to the blood and the time interval at which the shear occurs determine the likelihood of hemolysis. Although no field-wide consensus has been reached, experimental work conducted by Leverett et al and Wurzinger et al are often cited and, consequently, data from these works were used to evaluate the performance of the present apparatus from a hemolysis standpoint.

After multiple iterations of CFD and topology modifications, the model was then rechecked against the Visual Human data for anatomical fit. If needed, adjustments were made to the topology to improve the anatomical fit and the design was then re-evaluated using CFD. This procedure was repeated until the apical cannula portion 18 of the inflow conduit 15 generally satisfied all anatomical and fluid performance requirements.

Another aspect of the present invention relates to the desirability to have the outer dimension of the apical cannula 18 maintain a circular cross-section through the heart wall. Although the inner topology followed is unique for the purpose of shaping the flow of blood, a circular outer topology through the heart wall can better ensure uniform sealing between the heart tissue and the outside of the apical cannula 18.

Pulsatile blood pumps typically operate in what is commonly referred to as "demand mode." More precisely, these pumps operate such that they pump blood only after the blood sac has filled completely. In this fashion, the pump does not pull blood out of the left ventricle, but rather allows the sac to be passively filled. A continuous flow pump, like that described in U.S. Pat. No. 5,928,131, requires a continuous supply of blood while operating. In fact, such pumps will actually create suction at the inlet end to draw in blood. Although extremely high levels of suction can directly damage a patient's blood, lower levels of suction can still collapse the heart and/or the inflow conduit. As a result of this, the control of a continuous flow pump is a key aspect in its successful performance as a safe and efficacious treatment method. In an embodiment of the invention, the apical cannula portion 18 of the inflow conduit 15 can be made of a stiff polyurethane, for instance, or could be reinforced with metal wire or metal rings. It is also feasible to construct the apical cannula 18 of a biocompatible metal, such as titanium or an alloy of titanium. In any case, it can be preferable to construct the apical cannula portion 18 of the inflow conduit 15 of a rigid material or have adequate structural members to withstand any possible changes in dimension.

Pressures or forces may also be exerted externally to the entire inflow conduit 15 or portions thereof. For the apical cannula portion 18, reinforcement to prevent collapse due to blood pump suction can preferably also be sufficient to withstand any externally applied loads from the heart muscle or other body structures. The vascular graft portion 20 can also be fortified by additional reinforcement to prevent collapse due to internal or external loads. This reinforcement may take a variety of configurations, the simplest of which can include the attachment of reinforcing rings 53 to the wall of the vascular graft 20, as shown in FIGS. 7a and 7b. Although the reinforcing rings 53 may be made of a variety of materials, use of a polyurethane can be preferred due to the ease with which a polyurethane ring 53 can be bonded to polyester, from which the graft portion 20 can easily be made.

Figure 8C:
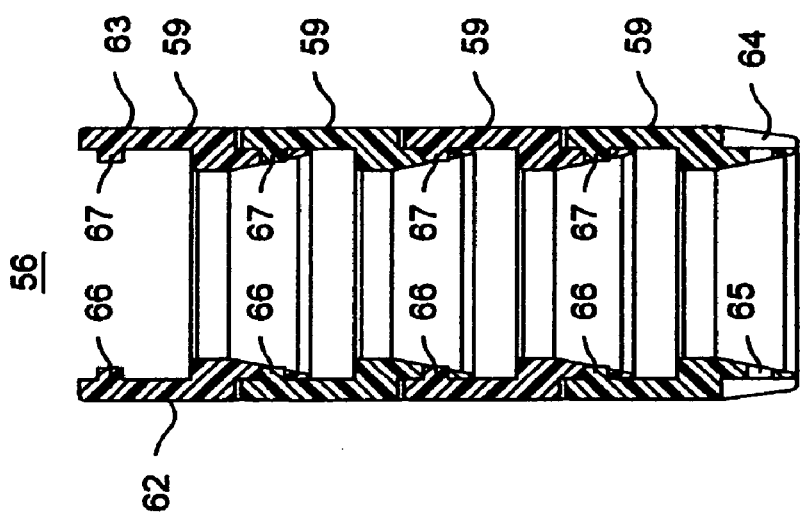
FIGS. 8a-8c illustrate an embodiment of reinforcement armor for a cannula.
Figure 8B:
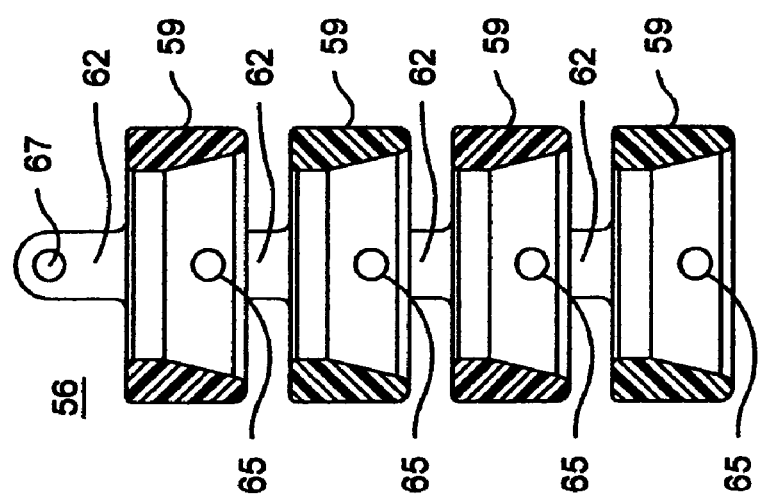
Figure 8A:
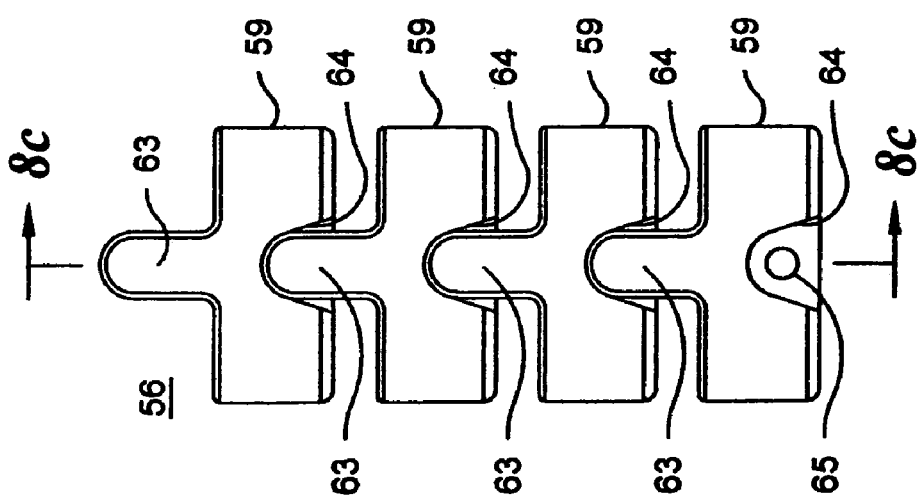

Another way to reinforce the vascular graft portion is shown in FIGS. 8a through 8c, and involves using a segmented armor 56 assembly. The armor assembly 56 can be a plurality of individual armor pieces 59 interconnected in a manner to form a hollow tubular member sized to surround a vascular graft portion. Each armor piece 59 can preferably be made of a polymer, such as polyurethane, and can have features that allow attachment of other armor pieces 59. Other polymers or metals can also be used depending on the needs of the invention. The armor pieces 59 can be interconnected in a manner to permit a limited amount of rotation therebetween such that a limited degree of flexing of the hollow tubular armor assembly, and thus also the vascular graft portion received therein, along a longitudinal axis thereof.

As seen best in FIG. 8c, two bosses 62, 63 extend from the generally cylindrical body of each armor piece 59. Each boss 62, 63 can have a small cylindrical nub, or pin, that extends off of the inner surface of the boss, towards the centerline of the armor piece. During assembly, the small nub on each boss of a single armor piece is press fit onto another armor piece. To facilitate this connection, a recessed channel 64 can be provided on each mating armor piece 59, as shown in FIGS. 9a-9b. Either the bosses 62, 63 and integral nubs 66, 67 may have a positional bias towards the centerline of the armor piece 59, or the recessed channel 64 on the mating armor piece 59 may be sloped with respect to the centerline of the armor piece 59. The angle of the boss 62, 63 or the recessed channel 64 may have a variety of values depending on the needs of the invention. In the embodiment shown, the channel 64 can be a generally parabolic shaped recessed area near the bottom of the armor piece 59, wherein the sides of the recessed channel limit the rotation of the boss 62, 63. In any instance, the purpose is to create a rotatable snap fit between mating armor pieces 59. The recessed channel 64 can have a small hole 65 for receiving the small nub 66, 67 of a mating armor piece 59. The fit of the small nub 66, 67 in the hole 65 can be such that rotation of one armor piece 59 relative to another is enabled.

Figure 9D:
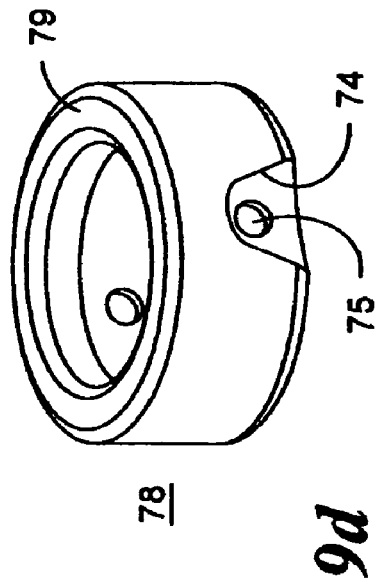
FIGS. 9a-9d are views, some in section, of individual armor pieces.
Figure 9C:
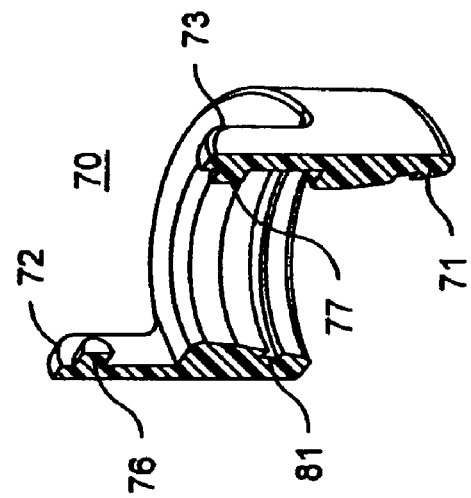
Figure 9A:
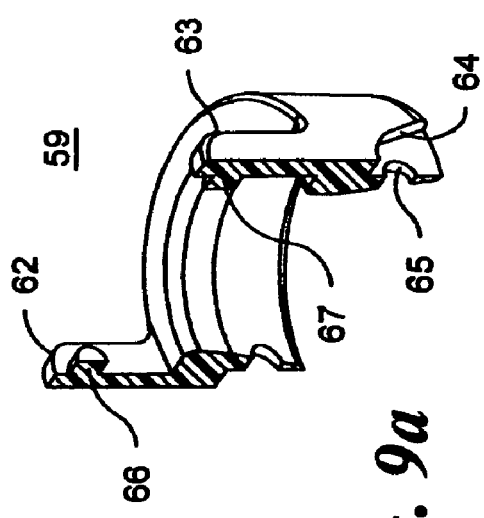
Figure 9B:
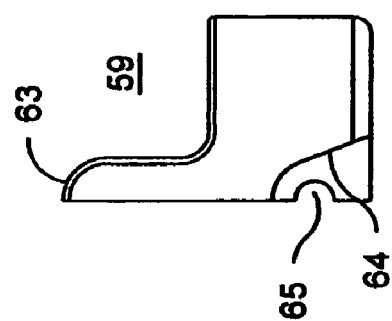

FIGS. 9c and 9d illustrate embodiments of armor end portions 70 and 78 of the cannula armor 56. One end portion 70 can have bosses 72, 73 with integral nubs 76, 78 which function the same as corresponding portions of the armor pieces 59. An opposite side 71 of the end portion 70 can be configured to attach to the inlet of a blood pump. An opposite end portion 78 can be configured to be positioned at the apical cannula 18 interface with the graft portion 20. One side of the end portion 70 can have a recessed angular channel 74 and small hole 75 which can function the same as corresponding portions on the armor pieces 59. An opposite side of the end portion 78 can be configured to cooperate with the adjacent end of the apical cannula 18 which attaches to the graft portion 20.

Figure 10A:
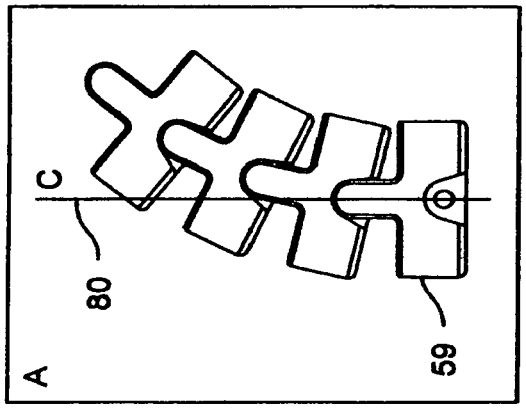
FIGS. 10a-10d illustrate bending of reinforcing armor pieces in FIG. 8a-8c in two planes.
Figure 10B:
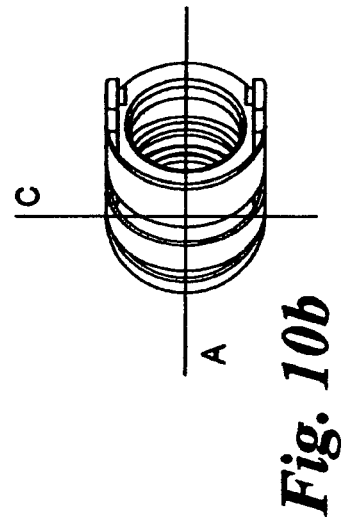
Figure 10C:
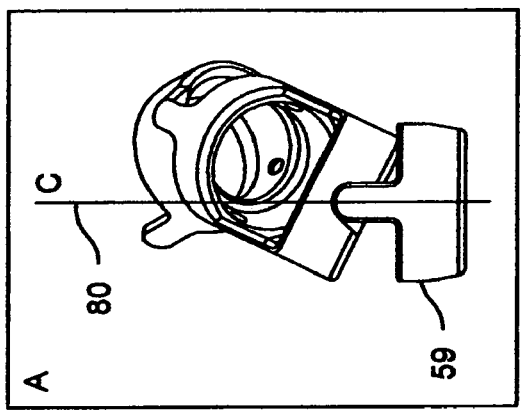
Figure 10D:
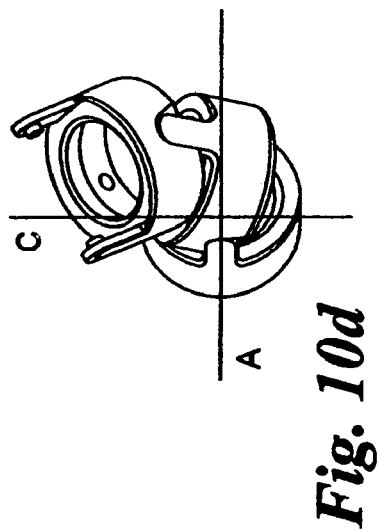

As stated above, the channel 64 that receives the nub of a mating armor piece 59 can be both recessed and angular. The angular aspect of the channel 64 can govern the angle that mating armor pieces 59 can have with respect to one another. As shown in FIGS. 10a and 10b, when viewed with respect to the centerline 80 of an armored piece 59, the angle can preferably be 20 degrees, which allows the mating pieces to have an angular position of ±20 degrees with respect to one another. The angular limitation allows great adjustability while preventing the graft portion 20 from obtaining a kink, which can adversely affect flow within the vascular graft 20 and become a site for subsequent tissue deposition. Moreover, the bosses 62, 63 of adjacent armor pieces 59 can lie along the centerline 80 such that the overall bending of the armoring 56 occurs in one plane only. In an alternative configuration depicted in FIGS. 10c and 10d, every other armor piece 59 could be provided with bosses 62, 63 positioned at ninety degrees (rotated) from the angular channels. When this type of armor piece configuration is used in an armor assembly, bending of the armor assembly in two planes is possible. This increases the adjustability of the conduit armor 56, which allows improved fitting of a blood pump within a patient's body.

On the armor piece 70 that can connect to the blood pump there can be provided an annular channel 81 that allows the armor piece 70 to rotate with respect to the blood pump connector, increasing the adjustability of the armor assembly 56. The use of the annular channel 81 for rotation can lessen the need for alternating armor pieces that with bosses oriented ninety-degrees rotationally from the recessed channel 64.

Figure 11B:
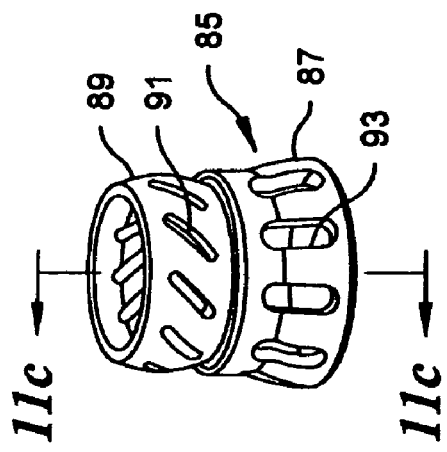
Figure 11C:
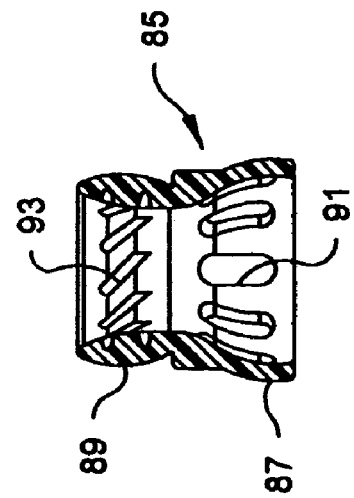
Figure 11A:
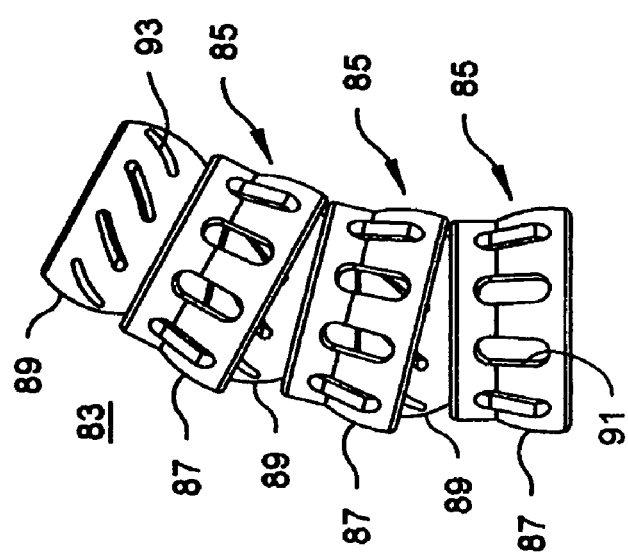

Another embodiment of a cannula armor assembly 83 that can be used is shown in FIGS. 11a-11c. In this embodiment, each armor piece 85 can have a larger bottom portion 87 that interlocks with the top portion 89 of another armor piece 85. The top portion 89 can have a partially spherical outer surface which is sized to be rotatably secured in a partially spherical inner surface of the bottom portion 87 of an adjacent armor piece 85. Depending on the radius of the top portion 89 and bottom portion 87 of the armor pieces 85, the armor assembly 83 can rotate freely without the restrictions inherent in the previous embodiment. In particular, no in-plane restriction exists for the relative rotation between armor pieces 85. In addition, although the previous armor assembly 56 can be configured to provide for bending of the armor assembly 56 in more than one plane, that configuration also inherently limits the possible rotation. For instance, the positioning of the boss 62, 63 relative to the angular recessed channel 64 only allows an additional degree of freedom between every other armor piece 59. Thus, two adjacent armor pieces 59 can still only have relative rotations in one plane. In the configuration of the armor pieces 85, adjacent armor pieces 85 can have limited rotation in any plane that the centerline of the armor piece 85 passes through.

Another feature illustrated with the armor pieces 85 is the use of holes 91, 93 or passages, across the thickness of the armor pieces 85. These holes 91, 93 can permit in-growth of tissue that is exterior to the armor pieces 85, into the vascular graft portion 20, which is how a neointima, or tissue lining, typically develops in a vascular graft. Some of these passages 91, 93 can also be used for sutures or other structural members that can provide radial support to the graft portion 20 for prevention of collapse due to negative blood pressure. The locations and shapes of the passages 91, 93 depicted in FIGS. 11a-11c could also be utilized with previous embodiments of conduit armor. Other passage shapes and sizes are easily conceivable to those skilled in the art.

Other features can be also used to augment the design of the inflow conduit 15. For instance, the apical cannula 18 of the inflow conduit 15 can preferably be secured to the patient's heart with a sewing cuff (not shown), in a manner known to those skilled in the art. The cuff can be situated around the straight region 30 of the apical cannula 18 and is preferably sutured to the heart muscle in a conventional manner. The sewing cuff may also serve a secondary purpose when used with a device such as outlined in U.S. Pat. Nos. 5,928,131 and 5,980,448. A defibrillation electrode can be incorporated into the sewing cuff, while another defibrillation lead can be placed elsewhere in or on the heart. The positioning of an electrode on the apex of the heart has various advantages. For instance, incorporation of the electrode into the sewing cuff eliminates one electrode from the two needed for defibrillation. While the use of a patch electrode on the apex has been shown as efficacious, patch electrodes have also been known to migrate over time. Instances of a patch moving across the epicardium (heart outer surface) or through the heart wall have been known. By attaching the electrode to the sewing cuff, and hence the inflow conduit, subsequent migration of the electrode is prevented. By combining a blood pump with a defibrillator, treatment of patients suffering from both congestive heart failure (CHF) and sudden cardiac death (SCD) is possible. SCD involves the occurrence of dangerous heart arrhythmias that result in a person's heart pumping an inadequate amount of blood. In the absence of CHF, many persons at a risk of sudden cardiac death have an implantable defibrillator installed to automatically treat the heart arrhythmias associated with SCD.

Referring now to FIG. 12, another aspect of the present invention can be the incorporation of a pressure sensor 100 into the apical cannula 18 which can be used to regulate blood pump output. It is possible to measure some small allowable dimensional change in the apical cannula 18 of the inflow conduit 15 for the purpose of measuring pressure within the inflow conduit 15. For instance, a support member, or ring 102 can be attached along the straight region 30 of the apical cannula 18 to which the strain or force-measuring sensor element 100 can be mounted. Preferably, the support ring 102 secures sensor 100 against the outer surface of the apical cannula 18. The sensor 100 can, for example, be a silicone-on-sapphire type sensing element or a standard strain-gage based or piezoelectric force sensor. In any case, small dimensional changes in the straight region 30 of the apical cannula 18 can be permitted in order to measure the internal pressure. The non-circular cross-section through the straight region 30 of the apical cannula 18 will tend to become more circular as the internal conduit pressure is increased. The support ring 102 can preferably be rigid enough to eliminate the possibility of circumferential stretching for the range of blood pressures that may be subjected to the inflow conduit 15. However, a higher level of rigidity can be needed to ensure no shape change occurs for the support ring 102 over the pressure range. The addition of the support ring 102 and integral sensor 100 allows local feedback on the pressure of blood entering the blood pump, which can be used to control the level of assist.

Figure 13C:
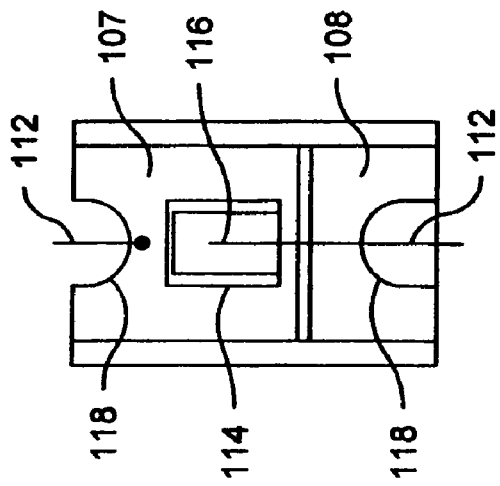
FIGS. 13a-13c illustrates an embodiment of a cannula according to the invention which can have a straight wall portion which an expand and contract.
Figure 13B:
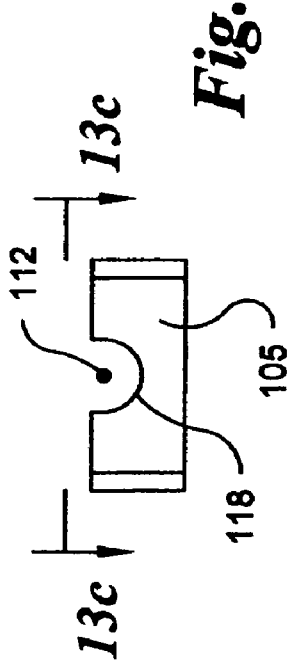
Figure 13A:
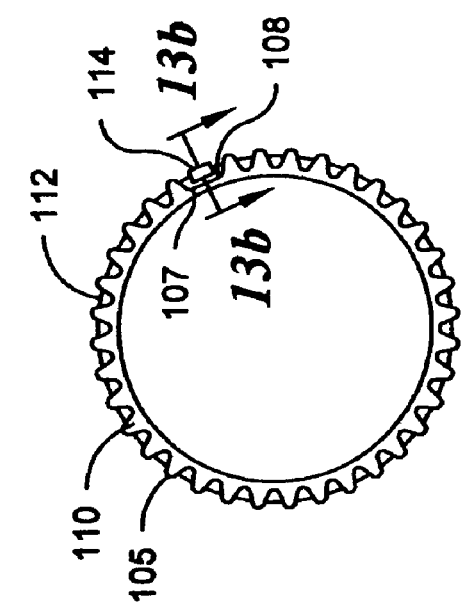

As illustrated in FIGS. 13a-13c, as opposed to adding stiffening elements, the straight region 30 of the apical cannula 18 can also have a thinner wall that expands and contracts in response to changes in conduit internal pressure. As shown in the cross section in FIG. 13a, to accomplish this, a corrugated metal strip 105 surrounds the apical cannula 18 before the one hundred twenty-degree bend, in the straight region 30. At either end, the corrugated strip 105 can have flat portions 107, 108. On one flat portion 107 of the corrugated strip 105, a metal wire 112 can be attached. At the opposite flat portion 108, a small metal end-housing 114 can be provided. The wire 112 can be wrapped around the full length of the metal strip 105, and the free-end 116 of the wire can terminate within, but not be attached to, the end-housing 114. The corrugated strip 105 can have notches 118 cut along the length thereof such that the wire 112 passes through the notches 118 over the length of the corrugated metal strip 105.

A spacer 110 can be situated between the wall of the inflow conduit 15 and the corrugated metal strip 105. The spacer 110 can be made from a silicone-elastomer spacer, and can partially fill the corrugations in the strip 105 to act as a softening element to avoid abrasion of the inflow conduit 15 by the metal strip 105.

As the pressure varies within the inflow conduit 15, the silicone-elastomer spacer 110 stretches and the metal strip 105 extends or "opens up." As a result of this, the end of the wire 112 moves relative to and within the end-housing 114. Consequently, this relative motion can be measured by using the wire 112 and end-housing 114 as a linearly variable displacement transducer (LVDT).

Although certain embodiments of the invention have been described in detail, it will be appreciated by those skilled in the art that various modifications to those details could be developed in light of the overall teaching of the disclosure. Accordingly, the particular embodiments disclosed herein are intended to be illustrative only and not limiting to the scope of the invention which should be awarded the full breadth of the following claims and any and all embodiments thereof.

What is claimed is:

1. An apical cannula member comprising:
    a. a first portion having a tip attachable to a heart ventricle;
    b. a second portion having a graft end connectable to a vascular graft member;
    c. a bend portion intermediate said tip and said graft end; and
    d. wherein said bend portion begins with a generally circular cross section, has a first transition to a cross section having a flattened oval shape, and then has a second transition from said flattened oval shape back to a generally circular cross section.

2. The apical cannula of claim 1 wherein said first transition further comprises said flattened oval shape characterized by a flattening of top and bottom sides of the apical cannula as defined by a plane through a centerline of said apical cannula.

3. The apical cannula of claim 2 wherein said second transition further comprises said flattened oval shape characterized by a flattening of left and right sides of the apical cannula, said left and right sides being perpendicular to said plane.

4. The apical cannula of claim 1 further comprising said first portion having a generally straight region between said tip and said bend portion, said generally straight region having a generally circular cross section.

5. The apical cannula of claim 4 further comprising said generally straight region having a decreasing diameter from said tip to said bend portion.

6. The apical cannula of claim 4 further comprising said generally straight region having a median diameter which is generally equal to a diameter of a hole which can be cored into said heart ventricle to accommodate insertion of said tip thereinto for attachment of said apical cannula.

7. The apical cannula of claim 6 further comprising said tip having a diameter which does not exceed said median diameter by more than about 0.5 centimeters.

8. The apical cannula of claim 4 further comprising said generally straight region having a generally circular cross section at least at along portion thereof which is insertable into said hole in said ventricle.

9. The apical cannula of claim 4 wherein said bend portion is substantially rigid.

10. The apical cannula member of claim 1 further comprising a pressure sensor attached to or incorporated into at least one of said first portion, said second portion, and said bend portion.

11. The apical cannula member of claim 10 further comprising a support ring which attaches to an outer surface of the apical cannula, said pressure sensor attached to said support ring and secured thereby to said outer surface.

12. The apical cannula of claim 11 wherein said support ring is attached to said first portion of said apical cannula.

13. The apical cannula member of claim 1 wherein at least one of said first and second portions has a wall portion which expands and contracts responsive to pressure changes in said apical cannula.

14. The apical cannula member of claim 13 wherein said wall portion further comprises:
    a. a thin inner wall member which stretches and contracts responsive said pressure; and
    b. a corrugated strip outer wall member which lengthens and shortens responsive to said pressure.

15. The apical cannula of claim 14 wherein said wall portion further comprises a spacer between said thin inner wall member and said corrugated strip outer wall member.

16. The apical cannula of claim 14 wherein said wall portion further comprises:
    a. said corrugated strip wall member having a first end and a second end, and notches therein between said first and second ends;
    b. an end-housing affixed to said second end of said corrugated strip wall member;

c. a wire having a fixed end attached to said first end of said corrugated strip wall member, said wire extending around said corrugated strip wall member through said notches, said wire having a free end movably disposed in said end-housing resulting in relative motion between said free end and said end-housing responsive to pressure changes in said apical cannula; and d. wherein said relative motion is measured using said free end and said end-housing as a linearly variable displacement transducer.

17. An apical cannula comprising:

a. a first portion having a tip attachable to a heart ventricle;

b. a second portion having a graft end connectable to a vascular graft member;

c. a bend portion intermediate said tip and said graft end; and d. at least one of said first and second portions has a wall portion which expands and contracts responsive to pressure changes in said apical cannula, wherein said wall portion further comprises:

e. a thin inner wall member which stretches and contracts responsive said pressure;

f. a corrugated strip outer wall member which lengthens and shortens responsive to said pressure; and g. a spacer between said thin inner wall member and said corrugated strip outer wall member.

18. An apical cannula of comprising:

a. a first portion having a tip attachable to a heart ventricle;

b. a second portion having a graft end connectable to a vascular graft member;

c. a bend portion intermediate said tip and said graft end; and d. at least one of said first and second portions has a wall portion which expands and contracts responsive to pressure changes in said apical cannula, wherein said wall portion further comprises:

e. a thin inner wall member which stretches and contracts responsive said pressure;

f. a corrugated strip outer wall member which lengthens and shortens responsive to said pressure, said corrugated strip wall member having a first end and a second end, and notches therein between said first and second ends;

g. an end-housing affixed to said second end of said corrugated strip wall member;

h. a wire having a fixed end attached to said first end of said corrugated strip wall member, said wire extending around said corrugated strip wall member through said notches, said wire having a free end movably disposed in said end-housing resulting in relative motion between said free end and said end-housing responsive to pressure changes in said apical cannula; and i. wherein said relative motion is measured using said free end and said end-housing as a linearly variable displacement transducer.

* * * * *